(12) United States Patent
Brown et al.

(10) Patent No.: US 6,274,577 B1
(45) Date of Patent: Aug. 14, 2001

(54) BENZODIAZEPINES

(75) Inventors: Julien Alistair Brown, Reading; Graham John Warrellow, Northwood; John Robert Porter, Chinnor; Sarah Catherine Archibald; John Clifford Head, both of Maidenhead, all of (GB)

(73) Assignee: Celltech Therapeutics Limited (GB)

( * ) Notice: Subject to any disclaimer, the term of this patent is extended or adjusted under 35 U.S.C. 154(b) by 0 days.

(21) Appl. No.: 09/408,258

(22) Filed: Sep. 29, 1999

(30) Foreign Application Priority Data

Sep. 30, 1998 (GB) .................................................. 9821222

(51) Int. Cl.[7] ........................ A61K 31/551; C07D 243/04

(52) U.S. Cl. ........................................... 514/221; 540/567

(58) Field of Search .............................. 540/567; 514/221

(56) References Cited

U.S. PATENT DOCUMENTS

| | | | |
|---|---|---|---|
| 4,470,973 | 9/1984 | Natarajan et al. | 424/177 |
| 4,554,273 | * 11/1985 | Bayssat et al. | |
| 4,987,132 | 1/1991 | Mase et al. | 514/252 |
| 5,164,372 | 11/1992 | Matsuo et al. | 514/19 |
| 5,227,490 | 7/1993 | Hartman et al. | 514/317 |
| 5,260,277 | 11/1993 | McKenzie | 544/18 |
| 5,296,486 | 3/1994 | Lazer et al. | 514/333 |
| 5,510,346 | * 4/1996 | Martin et al. | |
| 5,698,691 | * 12/1997 | Yukimasa et al. | |
| 5,773,646 | 6/1998 | Michael et al. | 562/439 |

FOREIGN PATENT DOCUMENTS

| | | |
|---|---|---|
| 23 16 881 | 10/1973 | (DE) . |
| 28 37 264 A1 | 3/1979 | (DE) . |
| 196 54 483 | 1/1998 | (DE) . |
| 0 031 104 A1 | 7/1981 | (EP) . |
| 0 048 763 A1 | 4/1982 | (EP) . |
| 0 144 230 | 6/1985 | (EP) . |
| 0 288 176 | 10/1988 | (EP) . |
| 0 322 068 A1 | 6/1989 | (EP) . |
| 0 394 989 A2 | 10/1990 | (EP) . |
| 0 498 268 A2 | 8/1992 | (EP) . |
| 0 596 406 A1 | 5/1994 | (EP) . |
| 0 710 657 A1 | 5/1996 | (EP) . |
| 0 710 659 A1 | 5/1996 | (EP) . |
| 0 842 943 A2 | 5/1998 | (EP) . |
| 0 842 945 A2 | 5/1998 | (EP) . |
| 56-090045 | 7/1981 | (JP) . |
| 3-135962 | 6/1991 | (JP) . |
| WO 86/02353 | 4/1986 | (WO) . |
| WO 93/00095 | 1/1993 | (WO) . |
| WO 93/08174 | 4/1993 | (WO) . |
| WO 93/09795 | 5/1993 | (WO) . |
| WO 94/15954 | 7/1994 | (WO) . |
| WO 94/15955 | 7/1994 | (WO) . |
| WO 94/29285 | 12/1994 | (WO) . |
| WO 95/13811 | 5/1995 | (WO) . |
| WO 95/15973 | 6/1995 | (WO) . |
| WO 95/19356 | 7/1995 | (WO) . |
| WO 95/35314 | 12/1995 | (WO) . |
| WO 96/01644 | 1/1996 | (WO) . |
| WO 96/22966 | 8/1996 | (WO) . |
| WO 96/26190 | 8/1996 | (WO) . |
| WO 97/03094 | 1/1997 | (WO) . |
| WO 97/08145 | 3/1997 | (WO) . |
| WO 97/12866 | 4/1997 | (WO) . |
| WO 97/31907 | 9/1997 | (WO) . |
| WO 97/36859 | 10/1997 | (WO) . |
| WO 98/00395 | 1/1998 | (WO) . |
| WO 98/04247 | 2/1998 | (WO) . |
| WO 98/04913 | 2/1998 | (WO) . |
| WO 98/42662 | 10/1998 | (WO) . |
| WO 98/53814 | 12/1998 | (WO) . |
| WO 98/53817 | 12/1998 | (WO) . |
| WO 98/53818 | 12/1998 | (WO) . |
| WO 98/54207 | 12/1998 | (WO) . |
| WO 98/58902 | 12/1998 | (WO) . |
| WO 99/06390 | 2/1999 | (WO) . |
| WO 99/06431 | 2/1999 | (WO) . |
| WO 99/06432 | 2/1999 | (WO) . |
| WO 99/06433 | 2/1999 | (WO) . |

(List continued on next page.)

OTHER PUBLICATIONS

Yanagisawa, H. et al., WO 97/37970, "Preparation of phenylalkylcarboxylic acid derivatives lowering blood sugar level," *Chemical Abstracts*, 1997, Abstract 127:307307, 4 pages.

(List continued on next page.)

*Primary Examiner*—Richard L. Raymond
(74) *Attorney, Agent, or Firm*—Woodcock Washburn Kurtz Mackiewicz & Norris LLP

(57) ABSTRACT

Benzodiazapine derivatives of formula (1) are described:

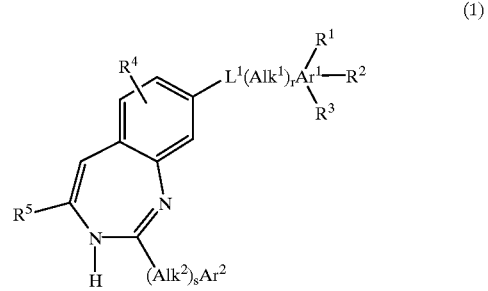

(1)

wherein

Ar$^1$ is an aromatic or heteroaromatic group;

L$^1$ is a linker atom or group;

Ar$^2$ is an optionally substituted aromatic or heteroaromatic group;

R$^5$ is a carboxylic acid (—CO$_2$H) or a derivative thereof;

The compounds are able to inhibit the binding of alpha 4 integrins to their ligands and are of use in the prophylaxis and treatment of immune in inflammatory disorders.

8 Claims, No Drawings

FOREIGN PATENT DOCUMENTS

| | | |
|---|---|---|
| WO 99/06434 | 2/1999 | (WO) . |
| WO 99/06435 | 2/1999 | (WO) . |
| WO 99/06436 | 2/1999 | (WO) . |
| WO 99/06437 | 2/1999 | (WO) . |
| WO 99/10312 | 3/1999 | (WO) . |
| WO 99/10313 | 3/1999 | (WO) . |
| WO 99/20272 | 4/1999 | (WO) . |
| WO 99/30709 | 6/1999 | (WO) . |
| WO 99/35163 | 7/1999 | (WO) . |
| WO 99/37618 | 7/1999 | (WO) . |
| WO 99/43642 | 9/1999 | (WO) . |
| WO 99/48879 | 9/1999 | (WO) . |
| WO 99/61465 | 12/1999 | (WO) . |

OTHER PUBLICATIONS

Lobb, R.R., et al., "Small molecule antagonists of alpha4 integrins: novel drugs for asthma," *Exp. Opin, Invest. Drugs*, 1999, XP000885957, 8(7), 935–945.

Samanen, J., et al., "Vascular indications for integrin alpha V antagonists," *Current Pharm. Design.*, 1997, 3, 545–584.

Šavrda, J., "CIS–TRANS isomerism of N–ACYL derivatives of proline and its analogues, linear peptides with CIS peptide bonds," Proc. 14$^{th}$ European Peptide Symposium, Loffet, A. (ed.), 1976, 653–656.

Azzouny, A.E., et al., "Synthesis of some N–substituted salicylamides structurally related to certain antimicrobials," *Pharmazie*, 1977, 32(6), 318–323 (abstract).

Badshah, A., et al., "Catalytic reduction of azlactones in alkaline media. Synthesis of amino acids," *J. of Organic Chemistry*, 1972, 37(18), 2916–2918.

Tous, G., et al., "O'–(Epoxyalkyl)tyrosines and (Epoxyalkyl)phenylalanine as irreversible inactivators of serine proteases: synthesis and inhibition mechanism," *J. of Medicinal Chemistry*, 1990, 33(6), 1620–1634.

Buckle, D.R., et al., "Non Thiazolidinedione Antihyperglycaemic Agents. 1: α–Heteroatom Substituted β–Phenylpropanoic Acids," *Bioorg. Med. Chem. Lett.*, 1996, 6(17), 2121–2126.

Keenan, R.M. et al., "Discovery of Potent Nonpeptide Vitronectin Receptor (av$\beta_3$) Antagonists," *J. Med. Chem.*, 1997, 40(15), 2289–2292.

McDowell, R.S. et al., "From Peptide to Non–Peptide. 2. The de Novo Design of Potent, Non–Peptidal Inhibitors of Platelet Aggregation Based on a Benzodiazepinedione Scaffold," *J. Am. Chem. Soc.*, 1994, 116, 5077–5083.

Miller, W.H. et al., "Structure–Activity Relationships in 3–Oxo–1,4–Benzodiazepine–2–Acetic Acid GPIIb/IIIa Antagonists. The 2–Benzazepine Series," *Bioorg. Med. Chem. Lett.*, 1996, 6(21), 2481–2486.

Ukai, Y. et al., "A novel synthetic inhibitor of endopeptidase–24.15," *Chemical Abstracts*, 1997, 127(2), 1 page.

Venturella, V.S. et al., "Substituted 1,3–Dihydro–4H–furo[3,4–d]–1,3–benzodiazepin–3–ones: Synthesis and Scope of the Method," *J. Heterocyclic Chem.*, 1969, 6(5), 671–679.

Wojciechowska, H. et al., "Preparation of 2,4–dinitrophenyl derivatives of tyrosine," *Chemical Abstracts*, 1968, 68(25), Abstract No. 114926r, 1 page.

Abraham, W.M. et al., "α$_4$–Integrins Mediate Antigen–Induced Late Bronchial Responses and Prolonged Airway Hyperresponsiveness in Sheep," *J. Clin. Invest.*, 1994, 93, 776–787.

Bach et al., "Anomalous optical rotation and circular dichroism of N–thioacylated.alpha.–amino acids and deriva," *Acta Chem. Scand.*, 1996, 20(10), 2781–2794.

Barrett, G.C., "Circular dichroism of N–thiobenzoly–1–α–amino acids. III. Their circular dichroism through the near–ultraviolet wavelength range," *J. Chem. Soc.*, 1967, Section C, 1–5.

Berlin, C. et al., "α4β7 Integrin Mediates Lymphocyte Binding to the Mucosal Vascular Addressin MAdCAM–1," *Cell*, 1993, 74, 185–195.

Binns, R.M. et al., "The Role of E–Selectin in Lymphocyte and Polymorphonuclear Cell Recruitment into Cutaneous Delayed Hypersensitivity Reactions in Sensitized Pigs," *J. Immunol.*, 1996, 157, 4094–4099.

Briskin, M.J. et al., "Structural Requirements for Mucosal Vascular Addressin Binding to Its Lymphocyte Receptor $\alpha_4\beta_7$," *J. Immunol.*, 1996, 156, 719–726.

Cardarelli, P.M. et al., "Cyclic RGD Peptide Inhibits α4β7 Interaction with Connecting Segment 1 and Vascular Cell Adhesion Molecule," *J. Biol. Chem.*, 1994, 269(28), 18668–18673.

*Chemical Abstracts*, "N–[4–Thiazolidinyl)carbonyl]amino acid derivatives," 1981, 95(19), Abstract No. 169173f, 1 page.

Corey, E.J. et al., "A Synthetic Method for Formyl→Ethynyl Conversion (RCHO→RC=CH or RC=CR')," *Tetrahedron Lett.*, 1972, 36, 3769–3772.

Cornforth, J.W., "Oxazoles and Oxazolones," *Chem. Penicillin*, Princeton Book Review, 1949, pp. 688, 799, and 800.

Ferguson, T.A. et al., "Two integrin–binding peptides abrogate T cell–mediated immune responses in vivo," *Proc. Natl. Acad. Sci. USA*, 1991, 88, 8072–8076.

Fu, H. et al., "Preliminary study on synthesis and antitumor activity in vitro of derivatives of timonacic," *Chemical Abstracts*, 1988, 108(17), Abstract No. 150358k, 1 page.

Harris, R.L.N. et al., *Aust. J. Chem.*, "Potential wool growth inhibitors. 2(1H)–Pyridone analogs of mimosine," 1977, 30(3), 649–655.

Hartke, K. et al., "Dithio and thiono esters. Part 61. Synthesis of α–amino dithioesters and endothiodipeptides,", *J. Prakt. Chem.*, 1996, 338(3), 251–256.

Holzmann, B. et al., "Peyer's patch–specific lymphocyte homing receptors consist of a VLA–4–like α chain associated with either of two integrin β chains, one of which is novel," *EMBO J.*, 1989, 8(6), 1735–1741.

Humphries, M.J. et al., "Mechanisms of VCAM–1 and fibronectin binding to integrin $\alpha_4\beta_1$: implications for integrin function and rational drug design," Ciba Foundation Symposium, 1995, 189, 177–194.

Issekutz, T.B., "Inhibition of Lymphocyte Endothelial Adhesion and In Vivo Lymphocyte Migration to Cutaneous Inflammation by TA–3, a New Monoclonal Antibody to Rat LFA–1," *J. Immunol.*, 1992, 149(10), 3394–3402.

Jaynes, B.H. et al., "Synthesis and In Vivo Antibacterial Activity of Hygromycin a Analogs Modified at the C$_{4'}$ Aryl Position," *Bioorg. Med. Chem. Letts.*, 1993, 3(8), 1531–1536.

Jepson, J.B. et al., "Reactions of α–Thioacylamino–acids. Their conversion into Thiazolones and Derivatives Thereof," *J. Chem. Soc.*, 1955, 1791–1797.

Lei, H. et al., "Efficient Synthesis of a Phosphinate Bis–Amino Acid and Its Use in the Construction of Amphiphilic Peptides," *J. Org. Chem.*, 1994, 59, 4206–4210.

Li, Z. et al., "Effect of an anti–Mo1 MAb on ozone–induced airway inflammation and airway hyperresponsiveness in dogs," *Am. J. Physiol.*, 1992, 263(6 Pt 1), L723–726.

Marlin, S.D. et al., "LFA–1 Immunodeficiency Disease," *J. Exp. Med.*, 1986, 164, 855–867.

Masahiko, N., Japanese Patent No. 57–080370 published May 19, 1982, "Alpha–Methylcinnamic Acid Derivative, its Preparation and Antilipemic Agent Containing the Same," *Patent Abstracts of Japan*, 1982, 1 page.

Nagasawa, H.T. et al., "β–Substituted Cysteines as Sequestering Agents for Ethanol–Derived Acetaldehyde in Vivo," *J. Med. Chem.*, 1987, 30, 1373–1378.

Noike, Y., "Synthesis pf Quinolizine Derivatives. VI. Synthesis of 3–Aminoquinolizines. (1). Synthesis of dl–3–Amino–, dl–3–epi–Amino–, and dl–3–epi–Dimethylaminoquinolizidines," *Yakugaku Zasshi*, 1959, 79(12), 1514–1518 (English summary included).

Ohki, S. et al., "Synthesis of quinolizine derivatives. V. Studies on Diastereoisomer of Ethyl 3–Quinolizidinecarboxylate," *Chem. Pharm. Bull.*, 1959, 7(6), 708–712.

Osborne, L., "Leukocyte Adhesion to Endothelium in Inflammation," *Cell*, 1990, 62, 3–6.

Osborn, L. et al., "Direct Expression Cloning of Vascular Cell Adhesion Molecule 1, a Cytokine–Induced Endothelial Protein that Binds to Lymphocytes," *Cell*, 1989, 59, 1203–1211.

Podolsky, D.K. et al., "Attenuation of Colitis in the Cotton–top Tamarin by Anti–α4 integrin Monoclonal Antibody," *J. Clin. Invest.*, 1993, 92, 373–380.

Schultz, Von O.–E. et al., "Analogos of nuleic acid based as antimetabolites," *Arzneimittel Forschung. Drug Res.*, 1967, 17(8), 1060–1064 (English summary included).

Shroff, H.N. et al., "Small Peptide Inhibitors of $\alpha_4\beta_7$ Mediated MAdCAM–1 Adhesion to Lymphocytes," *Barge. Med. Chem. Letts.*, 1996, 6(21), 2495–2500.

Sonnenberg, A., "Integrins and Their Ligands," *Curr. Topics Microbiol. Immunol.*, 1993, 184, 7–35.

Springer, T.A., "Adhesion receptors of the immune system," *Nature*, 1990, 346, 425–434.

Springer, T.A., "Traffic Signals for Lymphocyte Recirculation and Leukocyte Emigration: The Multistep Paradigm," *Cell*, 1994, 76, 301–314.

Tsunematsu, H. et al., "Hydrolysis of phenylthiazolones of p–guanidinophenylalanine and arginine by trypsin and related enzymes," *J. Biochem.*, 1983, 94(4), 1119–1125.

Vanderslice, P. et al., "A Cyclic Hexapeptide is a Potent Antagonist of α4 Integrins," *J. Immunol.*, 1997, 158, 1710–1718.

Yang, X., "A predominant role of integrin α4 in the spontaneous development of autoimmune diabetes in nonobese diabetic mice," *Proc. Natl. Acad. Sci. USA*, 1994, 91, 12604–12608.

Yednock, T.A., "Prevention of experimental autoimmune encephalomyelitis by antibodies against α4β1 integrin," *Nature*, 1992, 356, 63–66.

Whitlock, B.J. et al., "Structure and synthesis of lathyrine," *J. Org. Chem.*, 1965, 30, 115–118.

WPI/Derwent No. XP–002076854, Japanese Patent No. JP 04 193 895 A (Ajinomoto, K.K.), Jul. 13, 1992, DW9234, 1 Page, Abstract Only.

WPI/Derwent No. XP–002076855, Japanese Patent No. JP 56 049 373 A (Dainippon Pharm Co Ltd), May 2, 1981, DW8125, 1 Page, Abstract Only.

Hammadi, A., et al., "Diastereoselective hydrogenation of monodehydro enkephalins controlled by chiral rhodium catalysts," *Tetrahedron: Asymmetry*, 1992, 3(10), XP002106601, 1247–1262.

Nunami, K., et al., "A novel synthesis of methyl 1,5–disubstituted imidazole–4–carboxylates using 3–bromo–2–isocyanoacrylates," *J. Org. Chem.*, 1994,59, XP002106602, 7635–7642.

Shimohigashi, Y., et al., "Dehydro–enkephalins," *Int. J. Peptide Protein Res.*, 1983, 21, XP002106600, 202–208.

Strange, P.G., et al., "Studies of enzyme–mediated reactions. Part II. Stereochemistry of the elimination of ammonia form L–tyrosine catalysed by the enzyme from maize," *J. Chem. Soc., Perkin I*, 1972, 18, XP002106603, 2364–2372.

WPI/Derwent No. XP002106604, Japanese Patent No. JP 60 190749 (Mitsui Toatsu Chem. Inc.), Sep. 28, 1985, 1 page, Abstract only.

* cited by examiner

BENZODIAZEPINES

This invention relates to a series of benzodiazepines, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T. A. Nature, 346, 425, (1990); Springer, T. A. Cell 76, 301, (1994)]. Many of these interactions are mediated by specific cell surface molecules collectively referred to as cell adhesion molecules.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 14 different integrin alpha chains and 8 different integrin beta chains have been identified [Sonnenberg, A. Current Topics in Microbiology and Immunology, 184, 7, (1993)]. The members of the family are typically named according to their heterodimer composition although trivial nomenclature is widespread in this field. Thus the integrin termed α4β1 consists of the integrin alpha 4 chain associated with the integrin beta 1 chain, but is also widely referred to as Very Late Antigen 4 or VLA4. Not all of the potential pairings of integrin alpha and beta chains have yet been observed in nature and the integrin family has been subdivided into a number of subgroups based on the pairings that have been recognised [Sonnenberg, A. ibid].

The importance of cell adhesion molecules in human leukocyte function has been further highlighted by a genetic deficiency disease called Leukocyte Adhesion Deficiency (LAD) in which one of the families of leukocyte integrins is not expressed [Marlin, S. D. et al J. Exp. Med. 164, 855 (1986)]. Patients with this disease have a reduced ability to recruit leukocytes to inflammatory sites and suffer recurrent infections which in extreme cases may be fatal.

The potential to modify adhesion molecule function in such a way as to beneficially modulate immune and inflammatory responses has been extensively investigated in animal models using specific monoclonal antibodies that block various functions of these molecules [e.g. Issekutz, T. B. J. Immunol. 3394, (1992); Li, Z. et al Am. J. Physiol. 263, L723, (1992); Binns, R. M. et al J. Immunol. 157, 4094, (1996)]. A number of monoclonal antibodies which block adhesion molecule function are currently being investigated for their therapeutic potential in human disease.

One particular integrin subgroup of interest involves the α4 chain which can pair with two different beta chains β1 and β7 [Sonnenberg, A. ibid]. The α4β1 pairing occurs on many circulating leukocytes (for example lymphocytes, monocytes and eosinophils) although it is absent or only present at low levels on circulating neutrophils. α4β1 binds to an adhesion molecule (Vascular Cell Adhesion Molecule-1 also known as VCAM-1) frequently up-regulated on endothelial cells at sites of inflammation [Osborne, L. Cell, 62, 3, (1990)]. The molecule has also been shown to bind to at least three sites in the matrix molecule fibronectin [Humphries, M. J. et al. Ciba Foundation Symposium, 189, 177, (1995)]. Based on data obtained with monoclonal antibodies in animal models it is believed that the interaction between α4β1 and ligands on other cells and the extracellular matrix plays an important role in leukocyte migration and activation [Yednock, T. A. et al, Nature, 356, 63, (1992); Podolsky, D. K. et al. J. Clin. Invest. 92, 373, (1993); Abraham, W. M. et al. J. Clin. Invest. 93, 776, (1994)].

The integrin generated by the pairing of α4 and β7 has been termed LPAM-1 [Holzmann, B and Weissman, I. EMBO J. 8, 1735, (1989)] and like α4β1, binds to VCAM-1 and fibronectin. In addition, α4β7 binds to an adhesion molecule believed to be involved in the homing of leukocytes to mucosal tissue termed MAdCAM-1 [Berlin, C. et al, Cell, 74, 185, (1993)]. The interaction between α4β7 and MAdCAM-1 may also be important at sites of inflammation outside of mucosal tissue [Yang, X-D. et al, PNAS, 91, 12604 (1994)].

Regions of the peptide sequence recognised by α4β1 and α4β7 when they bind to their ligands have been identified. α4β1 seems to recognise LDV, IDA or REDV peptide sequences in fibronectin and a QIDSP sequence in VCAM-1 [Humphries, M. J. et al, ibid] whilst α4β7 recognises a LDT sequence in MAdCAM-1 [Briskin, M. J. et al, J. Immunol. 156, 719, (1996)]. There have been several reports of inhibitors of these interactions being designed from modifications of these short peptide sequences [Cardarelli, P. M. et al J. Biol. Chem. 269, 18668, (1994); Shroff, H. N. Bioorganic. Med. Chem. Lett. 6, 2495, (1996); Vanderslice, P. J. Immunol. 158, 1710, (1997)]. It has also been reported that a short peptide sequence derived from the α4β1 binding site in fibronectin can inhibit a contact hypersensitivity reaction in a trinitrochlorobenzene sensitised mouse [Ferguson, T. A. et al, PNAS 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family it is very important to be able to identify selective inhibitors of the alpha 4 subgroup.

We have now found a group of compounds which are potent and selective inhibitors of α4 integrins. Members of the group are able to inhibit α4 integrins such as α4β1 and/or α4β7 at concentrations at which they generally have no or minimal inhibitory action on α integrins of other subgroups. The compounds are thus of use in medicine, for example in the prophylaxis and treatment of immune or inflammatory disorders as described hereinafter.

Thus according to one aspect of the invention we provide a compound of formula (1):

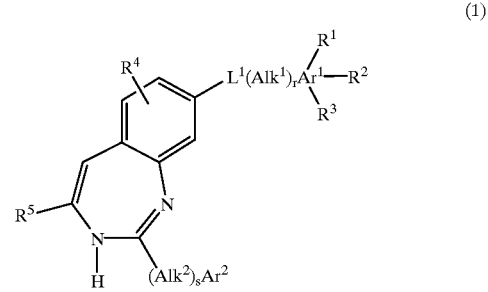

wherein $Ar^1$ is an aromatic or heteroaromatic group;

$R^1$, $R^2$, $R^3$ and $R^4$ which may be the same or different is each an atom or group —$L^2(Alk^3)_tL^3(R^6)_u$ in which $L^2$ and $L^3$ which may be the same or different is each a covalent bond or a linker atom or group, t is zero or the integer 1, u is an integer 1, 2 or 3, $Alk^3$ is an aliphatic or heteroaliphatic chain and $R^6$ is a hydrogen or halogen atom or a group selected from alkyl, —OR$^7$ [where R$^7$ is a hydrogen atom or an optionally substituted alkyl group], —SR$^7$, —NR$^7$R$^8$ [where R$^8$ is as just defined for R$^7$ and may be the same or different], —NO$_2$, —CN, —CO$_2$R$^7$, —SO$_3$H, —SOR$^7$, —SO$_2$R$^7$, —OCO$_2$R$^7$, —CONR$^7$R$^8$, —OCONR$^7$R$^8$, —CSNR$^7$R$^8$, —COR$^7$, —OCOR$^7$, —N(R$^7$)COR$^8$, —N(R$^7$)CSR$^8$, —SO$_2$ N(R$^7$)(R$^8$), —N(R$^7$)SO$_2$R$^8$, —N(R$^7$)CON(R$^8$)(R$^9$), [where R$^9$ is a hydrogen atom or an optionally substituted alkyl group]—N(R$^7$)CSN (R$^8$)(R$^9$), —N(R$^7$)SO$_2$N(R$^8$)(R$^9$) or —C(=NOR$^6$)R$^7$;

Alk$^1$ is an optionally substituted aliphatic or heteroaliphatic chain;

r is zero or the integer 1;

s is zero or the integer 1;

Alk$^2$ is —CH$_2$—, —(CH$_2$)$_2$— or —CH(CH$_3$)—;

L$^1$ is a linker atom or group;

R$^5$ is a carboxylic acid (—CO$_2$H) or a derivative thereof;

Ar$_2$ is an optionally substituted aromatic or heteroaromatic group;

and the salts, solvates, hydrates and N-oxides thereof.

In the compounds of formula (1), derivatives of the carboxylic acid group R$^5$ include carboxylic acid esters and amides. Particular esters and amides include —CO$_2$Alk$^5$ and —CONR$^7$R$^8$ groups as described herein.

In general, the substituents R$^1$, R$^2$ and R$^3$ in compounds of the invention ay be positioned on any available carbon atom, or, when present, itrogen atom in the aromatic or heteroaromatic group represented by Ar$^1$.

When Alk$^1$ in compounds of formula (1) is an optionally substituted aliphatic chain it may be an optionally substituted C$_{1-10}$ aliphatic chain. Particular examples include optionally substituted straight or branched chain C$_{1-6}$ alkyl, C$_{2-6}$ alkenyl, or C$_{2-6}$ alkynyl chains.

Heteroaliphatic chains represented by Alk$^1$ include the aliphatic chains just described but with each chain additionally containing one, two, three or four heteroatoms or heteroatom-containing groups. Particular heteroatoms or groups include atoms or groups L$^4$ where L$^4$ is as defined above for L$^1$ when L$^1$ is a linker atom or group. Each L$^4$ atom or group may interrupt the aliphatic chain, or may be positioned at its terminal carbon atom to connect the chain to an adjoining atom or group.

Particular examples of aliphatic chains represented by Alk$^1$ include optionally substituted —CH$_2$—, —CH$_2$CH$_2$—, —CH(CH$_3$)—, —C(CH$_3$)$_2$—, —(CH$_2$)$_2$CH$_2$—, —CH(CH$_3$)CH$_2$—, —(CH$_2$)$_3$CH$_2$—, —CH(CH$_3$)CH$_2$CH$_2$—, —CH$_2$CH(CH$_3$)CH$_2$—, —C(CH$_3$)$_2$CH$_2$—, —(CH$_2$)$_4$CH$_2$—, —(CH$_2$)$_5$CH$_2$—, —CHCH—, —CHCHCH$_2$—, —CH$_2$CHCH—, —CHCHCH$_2$CH$_2$—, —CH$_2$CHCHCH$_2$—, —(CH$_2$)$_2$CHCH—, —CC—, —CCCH$_2$—, —CH$_2$CC—, —CCCH$_2$CH$_2$—, —CH$_2$CCCH$_2$—, or —(CH$_2$)$_2$CC— chains. Where appropriate each of said chains may be optionally interrupted by one or two atoms and/or groups L$^4$ to form an optionally substituted heteroaliphatic chain. Particular examples include optionally substituted —L$^4$ CH$_2$—, —CH$_2$L$^4$CH$_2$—, —L$^4$(CH$_2$)$_2$—, —CH$_2$L$^4$(CH$_2$)$_2$—, —(CH$_2$)$_2$L$^4$CH$_2$—, —L$^4$(CH$_2$)$_3$— and —(CH$_2$)$_2$L$^4$(CH$_2$)$_2$— chains. The substituents which may be present on aliphatic or heteroaliphatic chains represented by Alk$^1$ include one, two, three or more substituents where each substituent may be the same or different and is selected from halogen atoms, e.g. fluorine, chlorine, bromine or iodine atoms, or C$_{1-6}$alkoxy, e.g. methoxy or ethoxy, thiol, C$_{1-6}$alkylthio e.g. methylthio or ethylthio, amino or substituted amino groups. Substituted amino groups include —NHR$^{11}$ and —N(R$^{11}$)$_2$ groups where R$^{11}$ is an optionally substituted straight or branched alkyl group as defined below for R$^9$. Where two R$^{11}$ groups are present these may be the same or different. Particular examples of substituted chains represented by Alk$^1$ include those specific chains just described substituted by one, two, or three halogen atoms such as fluorine atoms, for example chains of the type —CH(CF$_3$)—, —C(CF$_3$)$_2$— —CH$_2$CH(CF$_3$)—, —CH$_2$C (CF$_3$)$_2$—, —CH(CF$_3$)— and —C(CF$_3$)$_2$CH$_2$—.

When in the compounds of formula (1) L$^1$, L$^2$ and/or L$^3$ is present as a linker atom or group it may be any divalent linking atom or group. Particular examples include —O— or —S— atoms or —C(O)—, —C(O)O—, —OC(O)—, —C(S)—, —S(O)—, —S(O)$_2$—, —N(R$^{10}$)— [where R$^{10}$ is a hydrogen atom or an optionally substituted alkyl group], —CON(R$^{10}$)—, —OC(O)N(R$^{10}$)—, —CSN(R$^{10}$)—, —N(R$^{10}$)CO—, —N(R$^{10}$)C(O)O—, —N(R$^{10}$)CS—, —S(O)$_2$N(R$^{10}$)—, —N(R$^{10}$)S(O)$_2$—, —N(R$^{10}$)CON (R$^{10}$)—, —N(R$^{10}$)CSN(R$^{10}$)—, or —N(R$^{10}$)SO$_2$N(R$^{10}$)— groups. Where the linker group contains two R$^{10}$ substituents, these may be the same or different.

When R$^6$ R$^7$, R$^8$, R$^9$ and/or R$^{10}$ in the compounds of formula (1) is an alkyl group it may be a straight or branched C$_{1-6}$alkyl group, e.g. a C$_{1-3}$alkyl group such as a methyl or ethyl group. Optional substituents which may be present on such groups include for example one, two or three substituents which may be the same or different selected from halogen atoms, for example fluorine, chlorine, bromine or iodine atoms, or hydroxy or C$_{1-6}$alkoxy e.g. methoxy or ethoxy groups.

When Alk$^3$ is present in the compounds of formula (1) as an aliphatic or heteroaliphatic chain it may be for example any of the above-mentioned C$_{1-10}$aliphatic or heteroaliphatic chains described for Alk$^1$. Halogen atoms represented by R$^6$ in compounds of the invention include fluorine, chlorine, bromine, or iodine atoms.

Examples of the substituents represented by R$^1$, R$^2$, R$^3$ and R$^4$ in compounds of formula (1) include atoms or groups —L$^2$Alk$^3$L$^3$R$^6$, —L$^2$Alk$^3$R$^6$, —L$^2$R$^6$, and —Alk$^3$R$^6$ wherein L$^2$, Alk$^3$, L$^3$ and R$^6$ are as defined above. Particular examples of such substituents include —L$^2$CH$_2$L$^3$R$^6$, —L$^2$CH(CH$_3$)L$^3$R$^6$, —L$^2$CH(CH$_2$)$_2$L$^3$R$^6$, —L$^2$CH$_2$R$^6$, —L$^2$CH(CH$_3$)R$^6$, —L$^2$(CH$_2$)$_2$R$^6$, —CH$_2$R$^6$, —CH(CH$_3$) R$^6$, —(CH$_2$)$_2$R$^6$ and —R$^6$ groups.

Thus each of R$^1$, R$^2$, R$^3$ and R$^4$ in compounds of the invention may be for 5 example a hydrogen atom, a halogen atom, e.g. a fluorine, chlorine, bromine or iodine atom, or a C$_{1-6}$alkyl, e.g. methyl, ethyl, n-propyl, i-propyl, n-butyl or t-butyl, C$_{1-6}$alkylamino, e.g. methylamino or ethylamino, C$_{1-6}$ hydroxyalkyl, e.g. hydroxymethyl or hydroxyethyl, carboxyC$_{1-6}$alkyl, e.g. carboxyethyl, C$_{1-6}$alkylthio e.g. methylthio or ethylthio, carboxyC$_{1-6}$alkylthio, e.g. carboxymethylthio, 2-carboxyethylthio or 3-carboxypropylthio, C$_{1-6}$alkoxy, e.g. methoxy or ethoxy, hydroxyC$_{1-6}$alkoxy, e.g. 2-hydroxyethoxy, haloC$_{1-6}$alkyl, e.g. trifluoromethyl, haloC$_{1-6}$alkoxy, e.g. trifluoromethoxy, C$_{1-6}$alkylamino, e.g. methylamino or ethylamino, amino (—NH$_2$), aminoC$_{1-6}$alkyl, e.g. aminomethyl or aminoethyl, C$_{1-6}$dialkylamino, e.g. dimethylamino or diethylamino, C$_{1-6}$alkylaminoC$_{1-6}$alkyl, e.g. ethylaminoethyl, C$_{1-6}$dialkylaminoC$_{1-6}$alkyl, e.g. diethylaminoethyl, aminoC$_{1-6}$alkoxy, e.g. aminoethoxy, C$_{1-6}$alkylaminoC$_{1-6}$alkoxy, e.g. methylaminoethoxy, C$_{1-6}$dialkylaminoC$_{1-6}$alkoxy, e.g. dimethylaminoethoxy, diethylaminoethoxy, diisopropylaminoethoxy, or dimethylaminopropoxy, nitro, cyano, amidino, hydroxyl (—OH), formyl [HC(O)—], carboxyl (—CO$_2$H), —CO$_2$Alk$^5$ [where Alk$^5$ is as defined below], C$_{1-6}$ alkanoyl e.g. acetyl, thiol (—SH), thioC$_{1-6}$alkyl, e.g. thiomethyl or thioethyl, sulphonyl (—SO$_3$H), C$_{1-6}$alkylsulphinyl e.g. methylsulphinyl, C$_{1-6}$alkylsulphonyl, e.g. methylsulphonyl, aminosulphonyl (—SO$_2$NH$_2$), C$_{1-6}$alkylaminosulphonyl, e.g. methylaminosulphonyl or ethylaminosulphonyl, C$_{1-6}$dialkylaminosulphonyl, e.g. dimethylaminosulphonyl or diethylaminosulphonyl, phenylaminosulphonyl, carboxamido (—CONH$_2$), C$_{1-6}$alkylaminocarbonyl, e.g. methylaminocarbonyl or ethylaminocarbonyl, C$_{1-6}$dialkylaminocarbonyl, e.g. dimethylaminocarbonyl or diethylaminocarbonyl, aminoC$_{1-6}$alkylaminocarbonyl, e.g. aminoethylaminocarbonyl, C$_{1-6}$dialkylaminoC$_{1-6}$alkylaminocarbonyl, e.g. diethylaminoethylaminocarbonyl, aminocarbonylamino, C$_{1-6}$alkylaminocarbonylamino, e.g. methylaminocarbonylamino or ethylaminocarbonyl-amino, C$_{1-6}$dialkylaminocarbonylamino, e.g. dimethylaminocarbonylamino or diethylaminocarbonylamino, C$_{1-6}$alkylaminocabonylC$_{1-6}$alkylamino, e.g. methylaminocarbonylmethylamino, aminothiocarbonylamino, C$_{1-6}$alkylaminothiocarbonylamino, e.g. methylaminothiocarbonylamino or ethylaminothiocarbonylamino, C$_{1-6}$dialkylaminothiocarbonylamino, e.g. dimethylaminothiocarbonylamino or diethylaminothiocarbonylamino, C$_{1-6}$alkylaminothiocarbonylC$_{1-6}$alkylamino, e.g. ethylaminothiocarbonylmethylamino, C$_{1-6}$alkylsulphonylamino, e.g. methylsulphonylamino or ethylsulphonylamino, C$_{1-6}$dialkylsulphonylamino, e.g. dimethylsulphonylamino or diethylsulphonylamino, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, C$_{1-6}$alkanoylamino, e.g. acetylamino, aminoC$_{1-6}$alkanoylamino e.g. aminoacetylamino, C$_{1-6}$dialkylaminoC$_{1-6}$alkanoylamino, e.g. dimethylaminoacetylamino, C$_{1-6}$ alkanoylaminoC$_{1-6}$alkyl, e.g. acetylaminomethyl, C$_{1-6}$alkanoylaminoC$_{1-6}$alkylamino, e.g. acetamidoethylamino, C$_{1-6}$alkoxycarbonylamino, e.g. methoxycarbonylamino, ethoxycarbonylamino or t-butoxycarbonylamino group.

Aromatic groups represented by the groups Ar$^1$ and/or Ar$^2$ in compounds of the invention include for example monocyclic or bicyclic fused ring C$_{1-6}$ aromatic groups, such as phenyl, 1- or 2-naphthyl, 1- or 2-tetrahydronaphthyl, indanyl or indenyl groups.

Heteroaromatic groups represented by the groups Ar$^1$ and/or Ar$^2$ in the compounds of formula (1) include for example C$_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused-ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N-C$_{1-6}$alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, benzothienyl, benzotriazolyl, indolyl, isoindolyl, benzimidazolyl, imidazo[1,2-a]pyridyl, benzothiazolyl, benzoxazolyl, benzopyranyl, [3,4-dihydro]benzopyranyl, quinazolinyl, quinoxalinyl, naphthyridinyl, pyrido[3,4-b]pyridyl, pyrido[3,2-b]pyridyl, pyrido[4,3-b]-pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Optional substituents which may be present on the aromatic or heteroaromatic groups represented by Ar$^2$ include one, two, three or more substituents, each selected from an atom or group R$^{12}$ in which R$^{12}$ is —R$^{12a}$ or —Alk$^4$(R$^{12a}$)$_m$, where R$^{12a}$ is a halogen atom, or an amino (—NH$_2$), substituted amino, nitro, cyano, amidino, hydroxyl (—OH), substituted hydroxyl, formyl, carboxyl (—CO$_2$H), esterified carboxyl, thiol (—SH), substituted thiol, —COR$^{13}$ [where R$^{13}$ is an —Alk$^4$(R$^{12a}$)$_m$, aryl or heteroaryl group], —CSR$^{13}$, —SO$_3$H, —SO$_2$R$^{13}$—SO$_2$NH$_2$, —SO$_2$NHR$^{13}$SO$_2$N(R$^{13}$)$_2$, —CONH$_2$, —CSNH$_2$, —CONHR$^{13}$, —CSNHR$^{13}$, —CON[R$^{13}$]$_2$, —CSN(R$^{13}$)$_2$, —N(R$^{10}$)SO$_2$R$^{13}$, —N(SO$_2$R$^{13}$)$_2$, —NH(R$^{10}$)SO$_2$NH$_2$, —N(R$^{10}$)SO$_2$NHR$^{13}$, —N(R$^{10}$)SO$_2$N(R$^{13}$)$_2$, —N(R$^{10}$)COR$^{13}$, —N(R$^{10}$)CON(R$^{13}$)$_2$, —N(R$^{10}$)CSN(R$^{13}$)$_2$, —N(R$^{10}$)CSR$^{13}$, —N(R$^{10}$)C(O)OR$^{13}$, —SO$_2$NHet$^1$[where —NHet$^1$ is an optionally substituted C$_{5-7}$cyclicamino group optionally containing one or more other —O— or —S— atoms or —N(R$^{10}$)—, —C(O)— or —C(S)— groups], —CONHet$^1$, —CSNHet$^1$, —N(R$^{10}$)SO$_2$NHet$^1$, —N(R$^{10}$)CONHet$^1$, —N(R$^{10}$)CSNHet$^1$, —SO$_2$N(R$^{10}$)Het$^2$[where Het$^2$ is an optionally substituted monocyclic C$_{5-7}$carbocyclic group optionally containing one or more —O— or —S— atoms or —N(R$^{10}$)—, —C(O)— or —C(S)— groups], —Het$^2$, —CON(R$^{10}$)Het$^2$, —CSN(R$^{10}$)Het$^2$, —N(R$^{10}$)CON(R$^{10}$)Het$^2$, —N(R$^{10}$)CSN(R$^{10}$)Het$^2$, aryl or heteroaryl group; Alk$^4$ is a straight or branched C$_{1-6}$alkylene, C$_{2-6}$alkenylene or C$_{2-6}$alkynylene chain, optionally interrupted by one, two or three —O— or —S— atoms or —S(O)$_n$[where n is an integer 1 or 2] or —N(R$^{14}$)— groups [where R$^{14}$ is a hydrogen atom or C$_{1-6}$alkyl, e.g. methyl or ethyl group]; and m is zero or an integer 1, 2 or 3. It will be appreciated that when two R$^{10}$ or R$^{13}$ groups are present in one of the above substituents, the R$^{10}$ or R$^{13}$ groups may be the same or different.

When in the group —Alk$^4$(R$^{12a}$)$_m$ m is an integer 1, 2 or 3, it is to be understood that the substituent or substituents R$^{12a}$ may be present on any suitable carbon atom in —Alk$^4$. Where more than one R$^{12a}$ substituent is present these may be the same or different and may be present on the same or different atom in —Alk$^4$. Clearly, when m is zero and no substituent R$^{12a}$ is present the alkylene, alkenylene or alkynylene chain represented by Alk$^4$ becomes an alkyl, alkenyl or alkynyl group.

When R$^{12a}$ is a substituted amino group it may be for example a group —nNHR$^{13}$ [where R$^{13}$ is as defined above] or a group —N(R$^{13}$)$_2$ wherein each R$^{13}$ group is the same or different.

When R$^{12a}$ is a halogen atom it may be for example a fluorine, chlorine, bromine, or iodine atom.

When R$^{12a}$ is a substituted hydroxyl or substituted thiol group it may be for example a group —OR$^{13}$ or a —SR$^{13}$ or —SC(=NH)NH$_2$ group respectively.

Esterified carboxyl groups represented by the group $R^{12a}$ include groups of formula —$CO_2Alk^5$ wherein $Alk^5$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyl-oxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^5$ group include $R^{12a}$ substituents described above.

When $Alk^4$ is present in or as a substituent it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N($R^{10}$)— groups.

Aryl or heteroaryl groups represented by the groups $R^{12a}$ or $R^{13}$ include mono- or bicyclic optionally substituted $C_{6-12}$ aromatic or $C_{1-9}$ heteroaromatic groups as described above for the group $Ar^2$. The aromatic and heteroaromatic groups may be attached to the remainder of the compound of formula (1) by any carbon or hetero e.g. nitrogen atom as appropriate.

When —$NHet^1$ or -$Het^2$ forms part of a substituent $R^{12}$ each may be for example an optionally substituted pyrrolidinyl, pyrazolidinyl, piperazinyl, morpholinyl, thiomorpholinyl, piperidinyl or thiazolidinyl group. Additionally $Het^2$ may represent for example, an optionally substituted cyclopentyl or cyclohexyl group. Optional substituents which may be present on —$NHet^1$ or —$Het^2$ include one, two or three substituents which may be the same or different and selected from halogen atoms, for example fluorine, chlorine, bromine or iodine atoms, or $C_{1-6}$alkyl, e.g. methyl or ethyl, $C_{1-6}$alkoxy, e.g. methoxy or ethoxy or hydroxy groups.

Particularly useful atoms or groups represented by $R^{12}$ include fluorine, chlorine, bromine or iodine atoms, or $C_{1-6}$alkyl, e.g. methyl, ethyl, n-propyl, i-propyl, n-butyl or t-butyl, optionally substituted phenyl, pyridyl, pyrimidinyl, pyrrolyl, furyl, thiazolyl, thienyl, morpholinyl, thiomorpholinyl, piperazinyl, pyrrolidinyl or piperidinyl, $C_{1-6}$alkylamino, e.g. methylamino or ethylamino, $C_{1-6}$hydroxyalkyl, e.g. hydroxymethyl or hydroxyethyl, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxypropylthio, $C_{1-6}$alkoxy, e.g. methoxy, ethoxy or propoxy, hydroxy$C_{1-6}$alkoxy, e.g. 2-hydroxyethoxy, optionally substituted phenoxy, pyridyloxy, thiazolyoxy, phenylthio or pyridylthio, $C_{5-7}$cycloalkoxy, e.g. cyclopentyloxy, halo$C_{1-6}$alkyl, e.g. trifluoromethyl, halo$C_{1-6}$alkoxy, e.g. trifluoromethoxy or difluoromethoxy, $C_{1-6}$alkylamino, e.g. methylamino, ethylamino or propylamino, amino (—$NH_2$), amino$C_{1-6}$alkyl, e.g. aminomethyl or aminoethyl, $C_{1-6}$dialkylamino, e.g. dimethylamino or diethylamino, amino$C_{1-6}$alkylamino e.g. aminoethylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, diisopropylaminoethoxy, or dimethylaminopropoxy, hydroxy$C_{1-6}$alkyl amino e.g. hydroxyethylamino or hydroxypropylamino, $Het^1NC_{1-6}$alkyl amino e.g. morpholinoproylamino or piperidinylethylamino, imido, such as phthalimido or naphthalimido, e.g. 1,8-naphthalimido, nitro, cyano, amidino, hydroxyl (—OH), formyl [HC(O)—], carboxyl (—$CO_2H$), —$CO_2Alk^5$ [where $Alk^5$ is as defined above], $C_{1-6}$ alkanoyl e.g. acetyl, optionally substituted benzoyl, thiol (—SH), thio$C_{1-6}$ alkyl, e.g. thiomethyl, thioethyl or thiopropyl, —SC(=NH)$NH_2$, sulphonyl (—$SO_3H$), $C_{1-6}$alkylsulphinyl, e.g. methylsulphinyl, ethylsulphinyl or propylsulphinyl, $C_{1-6}$ alkylsulphonyl, e.g. methylsulphonyl, ethylsulphonyl or propylsulphonyl, aminosulphonyl (—$SO_2NH_2$), $C_{1-6}$ alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—$CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$dialkylamino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, —CONHC(=NH)$NH_2$, $C_{1-6}$alkylsulphonylamino, e.g. methylsulphonylamino or ethylsulphonylamino, $C_{1-6}$ dialkylsulphonylamino, e.g. dimethylsulphonylamino or diethylsulphonylamino, optionally substituted phenylsulphonylam ino, aminosulphonylamino (—$NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, optionally substituted morpholinesulphonylamino or morpholinesulphonyl$C_{1-6}$alkylamino, optionally substituted phenylaminosulphonylamino, $C_{1-6}$alkanoylamino, e.g. acetylamino, amino$C_{1-6}$alkanoyl-amino e.g. aminoacetylamino, $C_{1-6}$dialkylamino$C_{1-6}$alkanoylamino, e.g. dimethylaminoacetylamino, $C_{1-6}$alkanoylamino$C_{1-6}$alkyl, e.g. acetylamin-methyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino or optionally substituted benzyloxy, benzylamino, pyridylmethoxy, thiazolylmethoxy, benzyloxycarbonylamino, benzyloxycarbonylamino$C_{1-6}$alkyl e.g. benzyloxycarbonylaminoethyl, benzothio, pyridylmethylthio or thiazolylmethylthio groups.

Where desired, two $R^{12}$ substituents may be linked together to form a cyclic group such as a cyclic ether, e.g. a $C_{1-6}$alkylenedioxy group such as methylenedioxy or ethylenedioxy.

It will be appreciated that where two or more $R^{12}$ substituents are present, these need not necessarily be the same atoms and/or groups. In general, the substituent(s) may be present at any available ring position in the aromatic or heteroaromatic group represented by $Ar^2$.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

In the compounds according to the invention the group $Ar^1$ is preferably a monocyclic aromatic or heteroaromatic group. Particularly useful groups of this type are phenyl groups or five- or six-membered heteroaromatic groups as described previously, especially five- or six-membered heteroaromatic groups containing one or two heteroatoms selected from oxygen, sulphur or nitrogen atoms. Nitrogen-containing groups are especially useful, particularly pyridyl or pyrimidinyl groups. $R^1$, $R^2$ and $R^3$ attached to these $Ar^1$ groups may each be a hydrogen atom or one of the other atoms or groups generally and particularly described above in relation to $R^1$, $R^2$ and $R^3$. Particularly useful atoms or groups include halogen atoms or alkyl, —$OR^7$, —$SR^7$, —$NR^7R^8$, —$NO_2$ or —CN groups as described above in relation to the compounds of formula (1).

A particularly useful group of compounds according to the invention has the formula (2):

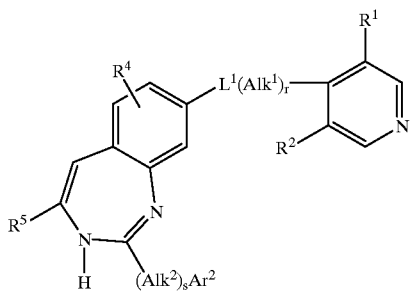

(2)

wherein $R^1$ and $R^2$, which may be the same or different is each an atom or group —$L^2(Alk^3)_tL^3(R^6)_u$ in which $L^2$, $Alk^3$, t, $L^3$, $R^6$ and u are as defined for formula (1) provided that $R^1$ and $R^2$ are not both hydrogen atoms; $Alk^1$, $Alk^2$, r, s, $L^1$, $R^4$, $R^5$ and $Ar^2$ are as defined for formula (1); and the salts, solvates, hydrates and N-oxides thereof.

$R^1$ and $R^2$ in compounds of formula (2) is each preferably as particularly described above for compounds of formula (1) other than a hydrogen atom. Particularly useful $R^1$ and $R^2$ substituents include halogen atoms, especially fluorine or chlorine atoms, or methyl, halomethyl, especially —$CF_3$, —$CHF_2$ or —$CH_2F$, methoxy or halomethoxy, especially —$OCF_3$, —$OCHF_2$ or —$OCH_2F$ groups.

$R^5$ in the compounds of formulae (1) and (2) is preferably a —$CO_2H$ group.

When present, the aliphatic chain represented by $Alk^1$ in compounds of formulae (1) and (2) is preferably a —$CH_2$— chain.

In general in compounds of formulae (1) and (2) —$(Alk^1)_rL^1$— is preferably —$CH_2O$— or —$CON(R^{10})$—.

$R^4$ in compounds of formulae (1) and (2) is preferably a hydrogen or halogen atom or an alkyl, —$OR^7$, —$NO_2$, —CN or —$NR^7R^8$ group.

In general in compounds of formulae (1) and (2) s is preferably zero.

Particularly useful classes of compounds according to the invention are those wherein $Ar^2$ is an optionally substituted monocyclic aromatic or heteroaromatic group, particularly a phenyl group. Especially useful heteroaromatic groups represented by $Ar^2$ include optionally substituted monocyclic nitrogen-containing heteroaromatic groups, particularly optionally substituted pyridyl, pyrimidinyl and triazinyl groups.

Optional substituents which may be present on preferred $Ar^2$ aromatic or heteroaromatic groups include one or two substituents selected from those $R^{12}$ substituents described above.

Particularly useful $R^{12}$ substituents include a halogen atom, especially fluorine or chlorine, optionally substituted morpholinyl, optionally substituted thiomorpholinyl, optionally substituted piperidinyl, optionally substituted pyrrolidinyl, optionally substituted piperazinyl, thio$C_{1-6}$alkyl, especially thiomethyl, thioethyl or thiopropyl, optionally substituted thiobenzyl, halo$C_{1-6}$alkyl, especially trifluoromethyl, $C_{1-6}$alkyloxy, especially methoxy, ethoxy or propoxy, optionally substituted benzyloxy, halo$C_{1-6}$alkoxy, especially trifluoromethoxy and difluoromethoxy, $C_{1-6}$alklyamino, especially propylamino, $C_{1-6}$dialkylamino, especially dimethylamino or diethylamino, optionally substituted benzylamino, amino$C_{1-6}$alkylamino, $Het^1NC_{1-6}$alkylamino, especially 3-morpholinopropylamino, optionally substituted phenoxy, hydroxy$C_{1-6}$alkylamino, nitro, carboxyl, —$CO_2Alk^5$ [where $R^5$ is as defined above], especially carboxymethyl and carboxyethyl, carboxamido, $C_{1-6}$alkylaminocarbonyl, $C_{1-6}$dialkylaminocarbonyl, $C_{1-6}$alkanoyl, optionally substituted benzoyl, $C_{1-6}$alkylsulphinoyl, $C_{1-6}$alkylsulphonyl, $C_{1-6}$alkylaminosulphonyl, $C_{1-6}$dialkylaminosulphonyl, $C_{1-6}$alkylaminocarbonyl and $C_{1-6}$dialkylamino-carbonyl.

Compounds according to the invention are potent and selective inhibitors of α4 integrins. The ability of the compounds to act in this way may be simply determined by employing tests such as those described in the Examples hereinafter.

A particularly useful compound according to the invention is:

2-(2-Chloro-3-pyridinyl)-9-[(3,5-dichloroisonicotinoyl)amino]-3H-1,3-benzodiazepine-4-carboxylic acid.

The compounds are of use in modulating cell adhesion and in particular are of use in the prophylaxis and treatment of diseases or disorders involving inflammation in which the extravasation of leukocytes plays a role and the invention extends to such a use and to the use of the compounds for the manufacture of a medicament for treating such diseases or disorders.

Diseases or disorders of this type include inflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds according to 10 the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $R^1$–$R^5$, $L^1$, $Alk^1$, $Alk^2$, r, s, $Ar^1$ and $Ar^2$ when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups. For convenience the processes described below all refer to a preparation of a compound of formula (1) but clearly the description applies equally to the preparation of compounds of formula (2).

Thus according to a further aspect of the invention, a compound of formula (1) in which $R^5$ is a —$CO_2H$ group may be obtained by hydrolysis of an ester of formula (3):

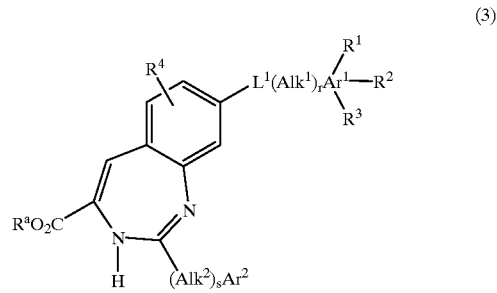

(3)

where $R^a$ is an alkyl group, for example a $C_{1-6}$alkyl group as described above.

The hydrolysis may be performed using either an acid or a base depending on the nature of $R^a$, for example an organic acid such as trifluoracetic acid or an inorganic base such as lithium, potassium or sodium hydroxide optionally in an aqueous organic solvent such as an amide, e.g. a substituted amide such as dimethylformamide, an ether, e.g. a cyclic ether such as tetrahydrofuran or dioxane or an alcohol, e.g. methanol at around ambient temperature. Where desired, mixtures of such solvents may be used.

Esters of formula (3) and, in general, esters of formula (1) in which R is a —$CO_2$ $Alk^5$ group may be prepared by cyclisation of an azide of formula (4):

(4)

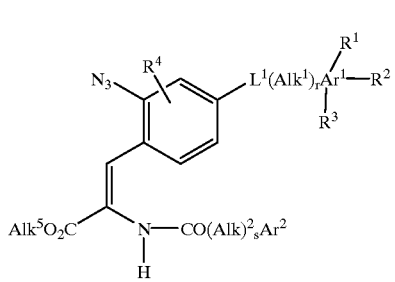

using a reducing agent such as a phosphine, e.g. triphenylphosphine or trimethylphosphine in an inert solvent, e.g. an aromatic hydrocarbon such as toluene, at an elevated temperature, e.g. the reflux temperature.

Azides of formula (4) are particularly useful intermediates and form a further feature of the invention.

Azides of formula (4) may be prepared by reaction of an aldehyde of formula (5):

(5)

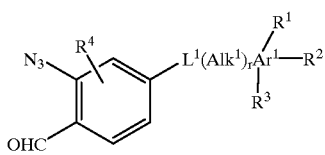

with a phosphonate $(Alk^6O)_2P(O)CH(NHCO(Alk^2)_sAr^2)CO_2Alk^5$, where $Alk^6$ is a $C_{1-6}$alkyl group optionally substituted by one or more fluorine atoms, in the presence of a base.

Suitable bases include organometallic bases, for example an organolithium compound such as n-butyllithium or lithium diisopropylamide, hydrides such as sodium or potassium hydride, alkoxides, such as sodium alkoxides, e.g. sodium methoxide, and cyclic amines, for example 1,8-diazabicyclo[5.4.0]undec-7-ene.

The reaction may be performed in a suitable solvent, for example a polar aprotic solvent such as an amide, e.g. N,N-dimethylformamide; or a nonpolar solvent such as an ether, e.g. a cyclic ether such as tetrahydrofuran or a halogenated hydrocarbon, e.g. dichloromethane. Preferably the reaction is carried out at a low temperature for example from around –78° C. to around ambient temperature.

Intermediate phosphonates of formula $(Alk^6O)_2P(O)CH(NHCO(Alk^2)_sAr^2)CO_2Alk^5$ are either known compounds or may be obtained by reaction of a halide $HalCH(NHCO(Alk^2)_sAr^2)CO_2Alk^5$ [where Hal is a halogen atom such as a chlorine or bromine atom] with a phosphite $P(OAlk^6)_3$. The halides $HalCH(NHCO(Alk^2)_sAr^2)CO_2Alk^5$ are either known compounds or may be prepared by manipulation of known compounds by the standard substitution, oxidation, reduction and/or cleavage reactions described hereinafter. In general the reaction with the phosphite $P(OAlk^6)_3$ may be carried out at any stage in the synthesis of the desired phosphonate $(Alk^6O)_2P(O)CH(NHCO(Alk^2)_sAr^2)CO_2Alk^5$.

Intermediate aldehydes of formula (5) may be obtained by oxidation of the corresponding alcohols of formula (6):

(6)

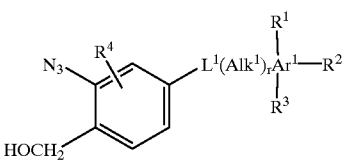

using an oxidising agent such as manganese (IV) oxide in a solvent such as dichloromethane.

The alcohols of formula (6) may be prepared by treatment of the corresponding amines of formula (7):

(7)

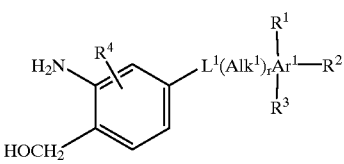

with a nitrite, e.g. sodium nitrite, in the presence of an acid such as hydrochloric acid at a low temperature e.g. around –5° C.; followed by reaction with an azide, e.g. sodium azide.

Where necessary, the intermediates of formulae (5), (6) and (7) may be obtained from simpler aromatic or heteroaromatic compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to modify the compounds of formula (1) and the esters (3) where appropriate functional groups exist in these compounds and to generate suitable phosphonates $(Alk^6O)_2P(O)CH(NHCO(Alk^2)_sAr^2)CO_2Alk^5$ for example to obtain desired groups $-CH(NHCO(Alk^2)_sAr^2)CO_2Alk^5$ therein.

Thus compounds of the invention and intermediates thereto may be prepared by alkylation, arylation or heteroarylation. For example, compounds containing a $-L^1H$, $-L^2H$, or $-L^3H$ group (where $L^1$, $L^2$ and $L^3$ (is each a linker atom or group) may be treated with an alkylating agent:

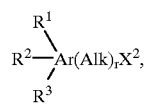

$R^6L^3Alk^3X^2$ or $R^{6a}X^2$ respectively in which $X^2$ is a leaving atom or group such as a halogen atom, e.g. a fluorine, bromine, iodine or chlorine atom or a sulphonyloxy group such as an alkylsulphonyloxy, e.g. trifluoromethylsulphonyloxy or arylsulphonyloxy, e.g. p-toluenesulphonyloxy group and $R^{6a}$ is an alkyl group.

The reaction may be carried out in the presence of a base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran.

In another example, compounds containing a $-L^1H$, $-L^2H$ or $-L^3H$ group as defined above may be functionalised by acylation or thioacylation, for example by reaction with one of the alkylating agents just described but in which $X^2$ is replaced by a —C(O)$X^3$, C(S)$X^3$, —N($R^7$)CO$X^3$ or —N($R^7$)C(S)$X^3$ group in which $X^3$ is a leaving atom or group as described for $X^2$. The reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature. Alternatively, the acylation or thioacylation may be carried out under the same conditions with an acid or thioacid (for example one of the alkylating agents described above in which $X^2$ is replaced by a —CO$_2$H or —COSH group) in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole. Alternatively the acid may be reacted with a chloroformate, for example ethylchloroformate, prior to the desired acylation reaction In a further example compounds may be obtained by sulphonylation of a compound containing an —OH group by reaction with one of the above alkylating agents but in which $X^2$ is replaced by a —S(O)Hal or —SO$_2$Hal group in which Hal is a halogen atom such as chlorine atom] in the presence of a base, for example an inorganic base such as sodium hydride in a solvent such as an amide, e.g. a substituted amide such as dimethylformamide at for example ambient temperature.

In another example, compounds containing a —$L^1$H, —$L^2$H or —$L^3$H group as defined above may be coupled with one of the alkylation agents just described but in which X is preplaced by an —OH group in a solvent such as tetrahydrofuran in the presence of a phosphine, e.g. triphenylphosphine and an activator such as diethyl, diisopropyl- or dimethylazodicarboxylate.

In a further example, ester groups —CO$_2$$R^7$ or —CO$_2$Alk$^5$ in the compounds may be converted to the corresponding acid [—CO$_2$H] by acid- or base-catalysed hydrolysis depending on the nature of the groups $R^7$ or Alk$^5$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a second example, —O$R^7$ or —O$R^{13}$ groups [where $R^7$ or $R^{13}$ each represents an alkyl grou p such as methyl group] in compounds of formula (1) may be cleaved to the corresp o n ding alcohol —OH by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding —OCH$_2$$R^{13}$ group (where $R^{13}$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be gene rated from the corresponding ester [—CO$_2$Alk$^5$ or CO$_2$$R^7$] or aldehyde [—CHO] by reduction, using for example a complex metal hydride such as lithium aluminium hydride o r sodium borohydride in a solvent such as methanol.

In another example, alcohol —OH groups in the compounds may be converted to a corresponding –O$R^7$ group by coupl ing with a reagent $R^7$OH in a solvent such as tetrahydrofuran in the presence of a phosphine, e.g. triphenylphosphine and an activator such as diethyl-, diisopropyl-, or dimethylazodicarboxylate.

Aminosulphonylamino [—NHSO$_2$NH$_2$] groups in the compounds may be obtained, in another example, by reaction of a corresponding amine [—NH$_2$] with sulphamide in the presence of an organic base such as pyridine at an elevated temperature, e.g. the reflux temperature.

In a further example amine (—NH$_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic aci d at arou nd ambient temperature.

In a further example, amine [—NH$_2$] groups in compounds of formula (1) may be obtained by hydrolysis from a corresponding imide by reaction with hydrazine in a solvent such as an alcohol, e.g. ethanol at ambient temperature.

In another example, a nitro [—NO$_2$] group may be reduced to an amine [—NH$_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, such as tin e.g. tin II chloride or iron, in the presence of an acid such as hydrochloric acid.

Aromatic halogen substituents in the compounds may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyidisulphide as the electrophile.

In another example, sulphur atoms in the compounds, for example when present in a linker group $L^1$, $L^2$ or $L^3$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suitable solvent or mixture of solvents e.g. an organic solvent such as an ether e.g. diethylether, or an alcohol, e.g. ethanol using conventional procedures.

The following Examples illustrate the invention. All temperatures are in ° C. The following abbreviations are used:

DMSO—dimethylsulphoxide; NMM—N-methylmorpholine;

DBU—1,8-diazabicyclo[5.4.0]undec-7-ene; MeOH—methanol;

All NMR's were obtained at 300 MHz.

INTERMEDIATE 1

2-Azido-4-nitrobenzyl alcohol

To a suspension of 2-amino-4-nitrobenzyl alcohol [(0.5 g) Bio. Org. Med. Chem (1995) 3, 2, 129] in concentrated hydrochloric acid/$H_2O$ (15 ml of 1:1 v:v) at −50 to 0° was added a solution of sodium nitrite (0.24 g) in water (2.5 ml) dropwise so the temperature did not rise above 0°. The mixture was stirred for 10 min, and added dropwise to a cooled (0°) solution of sodium acetate (3.0 g) and sodium azide (0.2 g) in water (10 ml). The resulting solid was filtered, washed with water and dried on the sinter to give the title compound as a pale brown powder (0.45 g, 78%). δH ($d_6$ DMSO): 4.51 (2H, s), 5.52 (1H, br), 7.72 (1H, d, J 8.4 Hz), 7.99 (1H, d, J 2.2 Hz) and 8.04 (1H, dd, J 2.2, 8.4 Hz).

INTERMEDIATE 2

2-Azido-4-nitrobenzaldehyde

To a solution of Intermediate 1 (0.6 g) in dichloromethane (100 ml) at room temperature was added manganese dioxide [<5 μ activated (6 g)] portionwise. The mixture was stirred for 90 min, filtered through a Celite® plug and concentrated in vacuo to give the title compound as a pale yellow solid (0.54 g, 91%). δH ($d_6$ DMSO): 8.05 (2H, s), 8.14 (1H, s) and 10.30 (1H,s).

INTERMEDIATE 3

N-(2-Chloronicotinovl)-α-phosphonoglycine trimethyl ester

A mixture of N-(benzyloxycarbonyl)-α-phosphonoglycine trimethyl ester (Aldrich, 4.86 g, 14.7 mmol) and palladium on charcoal (10% Pd, 2 g) in MeOH (60 ml) was stirred under a hydrogen atmosphere (balloon) for 4 h. The mixture was filtered through Celite® and the filtrate evaporated under reduced pressure to give the corresponding amine. 2-Chloronicotinoyl chloride (14.7 mmol, 2.59 g) was added to a solution of the amine and NMM (1.65 ml, 15 mmol) in $CH_2Cl_2$ (75 ml) at 0°. The mixture was stirred overnight at room temperature, diluted with $CH_2Cl_2$ (300 ml), washed with dilute hydrochloric acid (50 ml) and saturated $NaHCO_3$ (50 ml), dried ($Na_2SO_4$) and evaporated under reduced pressure to give the title compound as a colourless viscous gum (4.54 g, 91%). δH (DMSO-$d^6$) 9.67 (1H, dd, J 8.9,. 2.8 Hz, CONH), 8.49 (1H, dd, J 4.8, 2.0 Hz, ArH), 7.82 (1H, dd, J 7.5, 2.0 Hz, ArH), 7.50 (1H, dd, J 7.5, 4.8 Hz), 5.28 (1H, dd, J 22.9, 8.9 Hz, CHα) and 3.82–3.73 (9H, m, $CO_2Me$ +P($OMe)_2$); m/z (ES+, 60V) 337 (MH)+.

INTERMEDIATE 4

Methyl (Z)-3-(2-azido-4-n itrophenyl)-2-{[(2-chloro-3-pyridinyl)-carbonyl]amino}-2-propenoate To a solution of Intermediate 3 (0.44 g) in dichloromethane (10 ml) at 0° was added Intermediate 2 (0.23 g) followed by DBU (0.18 ml) dropwise. After stirring at this temperature for 1 h the mixture was partitioned between diethyl ether (100 ml) and water (50 ml). The aqueous layer was separated and the organics washed with water (4×50 ml), brine (50 ml), dried ($MgSO_4$), filtered and concentrated in vacuo to give the title compound as a pale yellow solid (0.42 g, 87%). δH ($d_6$ $CDCl_3$): 3.94 (3H, s), 7.34 (1H, dd, J 4.8, 7.6 Hz), 7.54 (1H, s), 7.59 (1H, d, J 8.6 Hz), 7.92 (1H, dd, J 8.5, 2.1 Hz), 7.99 (1H, d, J 7.1 Hz), 8.06 (1H, d, J 2.1 Hz) and 8.50 (2H, dd, 4.6, 2.0 Hz). m/z (ES+, 60V) 403 (MH)+.

INTERMEDIATE 5

Methyl 2-(2-chloro-3-pyridinyl)-8-nitro-3H-1,3-benzodiazepine-4-carboxylate

To a solution of Intermediate 4 (3.92 g) in toluene (250 ml) at 0° was added triphenylphosphine (2.6 g). The mixture was allowed to warm to room temperature and stirred overnight. The resulting suspension was heated at reflux for 24 h and then cooled to room temperature and concentrated to approximately 50 ml. The precipitated solid was filtered and dried on the sinter to give the title compound as a dark red solid (2.8 g, 80%). δH ($CDCl_3$): 3.84 (3H, s), 6.15 (1H, s), 6.37 (1H, br), 6.70 (1H, d, J 8.3 Hz), 7.32 (1H, dd, J 4.8, 7.5 Hz), 7.47 (1H, d, J 2.2 Hz), 7.67 (1H, dd, J 2.3, 8.3 Hz), 7.87 (1H, dd, J 1.9, 7.6 Hz) and 8.46 (1H, dd, J 1.9, 4.8 Hz). m/z (ES+, 60V) 359 (MH)+.

INTERMEDIATE 6

Methyl 8-amino-2-(2-chloro-3-pyridinyl)-3H-1.3-benzodiazepine-4-carboxylate

To a solution of Intermediate 5 (0.25 g) in methanol (50 ml) at room temperature was added tin (II) chloride dihydrate (0.79 g). The mixture was stirred overnight and then concentrated in vacuo. The residue was dissolved in dichloromethane (10 ml) and partitioned between ethyl acetate (150 ml) and sodium carbonate (100 ml, 15% aq). The mixture was stirred for 30 min, the organics were separated, washed with sodium carbonate (100 ml, 15% aqueous), brine (100 ml), dried ($MgSO_4$), filtered and solvent removed in vacuo to give the title compound as a dark red solid (0.12 g, 52%). δ0 H (DMSO $d_6$): 3.69 (3H, s), 5.98 (1H, br), 6.13 (1H, d, J 8.1 Hz), 6.57 (1H, s), 6.62 (1H, d, J 8.3 Hz), 7.46 (1H, dd, J 4.8, 7.4 Hz), 7.89 (1H, s), 7.77 (1H, d, J 5.8 Hz), 8.44 (2H, br) and 8.66 (1H, s). m/z (ES+, 60V) 329 (MH)+.

EXAMPLE 1

Methyl 2-(2-chloro-3-pyridinyl)-8-[(3.5-dichloroisonicotinoyl)amino]-3H-1.3-benzodiazepine-4-carboxylate To a solution of Intermediate 6 (0.12 g) in dichloromethane (5 ml) at 0° was added triethylamine (0.07 ml) and then a solution of 2,6-dichloroisonicotinoyl chloride (80 mg) in dichloromethane (1 ml). The reaction was concentrated in vacuo at 40°. This operation was repeated twice. The reaction mixture was partitioned between ethyl acetate (100 ml) and water (50 ml), the organics were separated and washed with water (50 ml), brine (50 ml), dried ($MgSO_4$) filtered and concentrated in vacuo to give a crude solid. This was subjected to column chromatography (EtOAc) to give the title compound as a red solid (0.14 g, 73%). δH (MeOH $d_4$) 3.78 (3H, s), 6.30–7.29 (4H, m), 7.43 (1H, dd, 7.6, 4.9 Hz), 7.88 (1H, t, J 7.9 Hz), 8.43 (1H, d, J 4.8 Hz), and 8.64 (2H, s). m/z (ES+, 60V) 502 (MH)+.

EXAMPLE 2

2-(2-Chloro-3-pyridinyl)-8-[(3.5-dichloroisonicotino)amino]-3H-1,3 -benzodiazepine-4-carboxylic acid To a solution of the compound of Example 1 (120 mg) in a mixture of THF (4 ml) and water (2 ml), was added LiOH.$H_2O$ (15 mg). The mixture was stirred for 3h, the organics were removed in vacuo and residue partitioned between ethyl acetate (15 ml) and sodium bicarbonate (15 ml saturated aqueous). The organics were separated and the aqueous layer extracted with ethyl acetate (2×10 ml), the combined organics were washed with water (15 ml), brine (15 ml), dried (MgSO$_4$), filtered and solvent removed in vacuo to give the title compound as a pale brown powder (35 mg, 30%). δH (DMSO d$_6$): 6.67 (1H, br), 6.84 (1H, br), 7.02 (1H, d, J 8.2 Hz), 7.46 (1H, dd, J 4.8, 7.6 Hz), 7.89 (1H, d, J 6.1 Hz), 8.44 (1H, dd, J 2.0, 4.8 Hz), 8.77 (21H, s) and 10.8 (1H, br). m/z (ES$^+$, 60V). 488 (MH)$^+$.

The following assays can be used to demonstrate the potency and selectivity of the compounds according to the invention. In each of these assays an IC$_{50}$ value was determined for each test compound and represents the concentration of compound necessary to achieve 50% inhibition of cell adhesion where 100%=adhesion assessed in the absence of the test compound and 0%=absorbance in wells that did not receive cells.

α$_4$β$_1$ Intearin-dependent Jurkat Cell Adhesion to VCAM-Ig 96 well NUNC plates were coated with F(ab)$_2$ fragment goat anti-human IgG Fcγ-specific antibody [Jackson Immuno Research 109-006-098: 100 μl at 2 μg/ml in 0.1M NaHCO$_3$, pH 8.4], overnight at 4°. The plates were washed (3×) in phosphate-buffered saline (PBS) and then blocked for 1 h in PBS/1% BSA at room temperature on a rocking platform. After washing (3×in PBS) 9 ng/ml of purified 2d VCAM-Ig diluted in PBS/1% BSA was added and the plates left for 60 minutes at room temperature on a rocking platform. The plates were washed (3×in PBS) and the assay then performed at 37° for 30 min in a total volume of 200 μl containing 2.5×10$^5$ Jurkat cells in the presence or absence of titrated test compounds.

Each plate was washed (2×) with medium and the adherent cells were fixed with 100 μl methanol for 10 minutes followed by another wash. 100 μl 0.25% Rose Bengal (Sigma R4507) in PBS was added for 5 minutes at room temperature and the plates washed (3×) in PBS. 100 μl 50% (v/v) ethanol in PBS was added and the plates left for 60 min after which the absorbance (570 nm) was measured.

α$_4$β$_7$ Integrin-dependent JY Cell Adhesion to MAdCAM-Ig

This assay was performed in the same manner as the α$_4$β$_1$ assay except that MAdCAM-Ig (150 ng/ml) was used in place of 2d VCAM-Ig and a sub-line of the β-lymphoblastoid cell-line JY was used in place of Jurkat cells. The IC$_{50}$ value for each test compound was determined as described in the α$_4$β$_1$ integrin assay.

α$_5$β$_1$ Intearin-dependent K562 Cell Adhesion to Fibronectin 96 well tissue culture plates were coated with human plasma fibronectin (Sigma F0895) at 5 μg/ml in phosphate-buffered saline (PBS) for 2 hr at 37° C. The plates were washed (3×in PBS) and then blocked for 1 h in 100 μl PBS/1% BSA at room temperature on a rocking platform. The blocked plates were washed (3×in PBS) and the assay then performed at 37° C. in a total volume of 200 μl containing 2.5×10$^5$ K562 cells, phorbol-12-myristate-13-acetate at 10 ng/ml, and in the presence or absence of titrated test compounds. Incubation time was 30 minutes. Each plate was fixed and stained as described in the α4β1 assay above.

α$_m$β$_2$-Dependent Human Polymorphonuclear Neutrophils Adhesion to Plastic 96 well tissue culture plates were coated with RPMI 1640/10% FCS for 2h at 37° C. 2×10$^5$ freshly isolated human venous polymorphonuclear neutrophils (PMN) were added to the wells in a total volume of 200 μl in the presence of 10 ng/ml phorbol-12-myristate-13-acetate, and in the presence or absence of test compounds, and incubated for 20 min at 37° C. followed by 30 min at room temperature. The plates were washed in medium and 100 μl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% H$_2$O$_2$ (Sigma) and 50 μg/ml TMB (Boehringer Mannheim) in 0.1M sodium acetate/citrate buffer, pH 6.0 and absorbance measured at 630 nm.

αIIb/$_3$-Dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of 6×10$^8$/ml in autologous plasma. Cuvettes contained equal volumes of PRP and filtered Tyrode's buffer (g/liter: NaCl 8.0; MgCl$_2$.H$_2$O 0.427; CaCl$_2$ 0.2; KCl 0.2; D-glucose 1.0; NaHCO$_3$ 1.0; NaHPO$_4$.2H$_2$O 0.065). Aggregation was monitored following addition of 2.5 μM ADP (Sigma) in the presence or absence of inhibitors.

In the above assays the preferred compounds of the invention generally have IC$_{50}$ values in the α$_4$β$_1$ and α$_4$β$_7$ assays of 1 μM and below. In the other assays featuring α integrins of other subgroups the same compounds had IC$_{50}$ values of 50 μM and above thus demonstrating the potency and selectivity of their action against α$_4$ integrins.

What is claimed is:

1. A compound of formula (1):

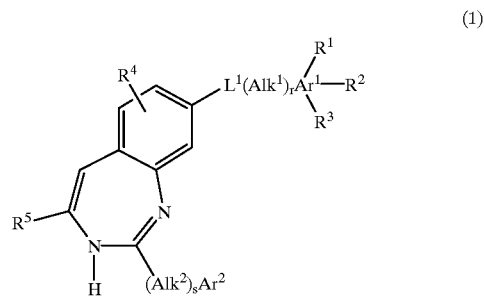

wherein Ar$^1$ is an aromatic or heteroaromatic group;

R$^1$, R$^2$, R$^3$ and R$^4$ which may be the same or different is each an atom or group —L$^2$(Alk$^3$)$_t$L$^3$(R$^6$)$_u$ in which L$^2$ and L$^3$ which may be the same or different is each a covalent bond or a linker atom or group selected from —O—, —S—, —C(O)—, —C(O)O—, —OC(O)—, —C(S)—, —S(O)—, —S(O)$_2$—, —N(R$^{10}$)— (where R$^{10}$ is a hydrogen atom or an optionally substituted alkyl group), —CON(R$^{10}$)—, —OC(O)N(R$^{10}$)—, —CSN(R$^{10}$)—, —N(R$^{10}$)CO—, —N(R$^{10}$)C(O)O—, —N(R$^{10}$)CS—, —S(O)$_2$N(R$^{10}$)—, —N(R$^{10}$)S(O)$_2$—, —N(R$^{10}$)CON(R$^{10}$)—, —N(R$^{10}$)CSN(R$^{10}$)—, and —N(R$^{10}$)SO$_2$N(R$^{10}$)—, t is zero or the integer 1, u is an integer 1, 2 or 3, Alk$^3$ is an aliphatic or heteroaliphatic chain and R$^6$ is a hydrogen or halogen atom or a group selected from alkyl, —OR$^7$ (where R$^7$ is a hydrogen atom or an optionally substituted alkyl group), —SR$^7$, —NR$^7$R$^8$, (where R$^8$ is as just defined for R$^7$ and may be the same or different), —NO$_2$, —CN, —CO$_2$R$^7$, —SO$_3$H, —SOR$^7$, —SO$_2$R$^7$, —OCO$_2$R$^7$, —CONR$^7$R$^8$, —OCONR$^7$R$^8$, —CSNR$^7$R$^8$, —COR$^7$, —OCOR$^7$, —N(R$^7$)COR$^8$, —N(R$^7$)CSR$^8$, —SO$_2$N(R$^7$)(R$^8$), —N(R$^7$)SO$_2$R$^8$, —N(R$^7$)CON(R$^8$)(R$^9$), (where R$^9$ is a hydrogen atom or an optionally substituted alkyl group) —N(R$^7$)CSN(R$^8$)(R$^9$), —N(R$^7$)SO$_2$N(R$^8$)(R$^9$) or —C(=NOR$^6$)R$^7$;

Alk$^1$ is an optionally substituted aliphatic or heteroaliphatic chain;

r is zero or the integer 1;

s is zero or the integer 1;

Alk$^2$ is —CH$_2$—, —(CH$_2$)$_2$— or —CH(CH$_3$)—;

L$^1$ is a linker atom or group selected from —O—, —S—, —C(O)—, —C(O)O—, —OC(O)—, —C(S)—, —S(O)—, —S(O)$_2$—, —N(R$^{10}$)— (where R$^{10}$ is a hydrogen atom or an optionally substituted alkyl group), —CON(R$^{10}$)—, —OC(O)N(R$^{10}$)—, —CSN(R$^{10}$)—, —N(R$^{10}$)CO—, —N(R$^{10}$)C(O)O—, —N(R$^{10}$)CS—, —S(O)$_2$N(R$^{10}$)—, —N(R$^{10}$)S(O)$_2$—, —N(R$^{10}$)CON(R$^{10}$)—, —N(R$^{10}$)CSN(R$^{10}$)—, and —N(R$^{10}$)SO$_2$N(R$^{10}$)—;

R$^5$ is a carboxylic acid (—CO$_2$H) or a derivative thereof;

Ar$^2$ is an optionally substituted aromatic or heteroaromatic group;

and the salts, solvates, hydrates and N-oxides thereof.

2. A compound according to claim 1 in which R$^5$ is a —CO$_2$H group.

3. A compound according to claim 1 in which s is zero.

4. A compound according to claim 1 in which Ar$^1$ is a phenyl, pyridyl or pyrimidinyl group, wherein R$^1$ and R$^2$ is each a halogen atom, or alkoxy or haloalkoxy group and R$^3$ is a hydrogen atom.

5. A compound according to claim 1 in which L$^1$ (Alk$^1$)$_r$ is a —OCH$_2$— or —N(R$^{11}$)CO— group.

6. A compound according to claim 1 in which Ar$^2$ is an optionally substituted phenyl, pyridyl, primidinyl or triazinyl group.

7. A compound which is:

2-(2-Chloro-3-pyridinyl)-8-[(3,5-dichloroisonicotinoyl)amino]-3H-1,3-benzodiazapine-4-carboxylic acid.

8. A pharmaceutical composition comprising a compound according to claim 1 together with one or more pharmaceutically acceptable carriers, excipients or diluents.

* * * * *

UNITED STATES PATENT AND TRADEMARK OFFICE
CERTIFICATE OF CORRECTION

PATENT NO.     : 6,274,577 B1
DATED          : August 14, 2001
INVENTOR(S)    : Brown et al.

It is certified that error appears in the above-identified patent and that said Letters Patent is hereby corrected as shown below:

<u>Column 3,</u>
Line 28, please delete "ay" and insert therefor -- may --;
Line 29, please delete "itrogen" and insert therefor -- nitrogen --;

<u>Column 4,</u>
Line 47, please delete "5";

<u>Column 5,</u>
Line 48, please delete "$C_{1-6}$" and insert therefor -- $C_{6-12}$ --;

<u>Column 6,</u>
Line 60, please delete "-nNHR$^{13}$" and insert therefor -- -NHR$^{13}$ --;

<u>Column 8,</u>
Line 43, please delete "phenylsulphonylam ino" and insert
therefor -- phenylsulphonylamino --;

<u>Column 11,</u>
Line 5, please delete "10";

<u>Column 15,</u>
Lines 51 & 52, please delete "corresp o n ding" and insert therefor -- corresponding --;
Line 64, please delete "o r" and insert therefor -- or --;

<u>Column 16,</u>
Line 1, please delete "coupl ing" and insert therefor -- coupling --;
Line 16, please delete "aci d" and insert therefor -- acid --;
Line 17, please delete "arou nd" and insert therefor -- around --;

<u>Column 17,</u>
Line 6, please delete "-50" and insert therefor -- 5°--;

<u>Column 17,</u>
Line 30, please delete "chloronicotinovl" and insert therefor -- chloronicotinoyl --;
Line 52, please delete "n itrophenyl" and insert therefor -- nitrophenyl --;

UNITED STATES PATENT AND TRADEMARK OFFICE
CERTIFICATE OF CORRECTION

PATENT NO.   : 6,274,577 B1
DATED        : August 14, 2001
INVENTOR(S)  : Brown et al.

It is certified that error appears in the above-identified patent and that said Letters Patent is hereby corrected as shown below:

Column 18,
Line 33, please delete "$\delta OH$" and insert therefor -- $\delta H$ --;
Line 61, please delete "dichloroisonicotino" and insert therefor
-- dichloroisonicotinoyl --;

Column 20,
Line 12, please delete "$\alpha IIB/_3$" and insert therefor -- $\alpha IIb/_3$ --;

Column 22,
Line 18, please delete "benzodizepine" and insert therefor -- benzodiazepine --.

Signed and Sealed this

Twenty-eighth Day of January, 2003

JAMES E. ROGAN
*Director of the United States Patent and Trademark Office*